United States Patent [19]
Rudt et al.

[11] Patent Number: 5,717,456
[45] Date of Patent: Feb. 10, 1998

[54] SYSTEM FOR MONITORING A CONTINUOUS MANUFACTURING PROCESS

[75] Inventors: Robert J. Rudt, Highland Mills, N.Y.; Leonard F. Fiore, Foley, Minn.; Kenneth D. Grapes, Indian Springs, Ohio

[73] Assignee: Champion International Corporation, Stamford, Conn.

[21] Appl. No.: 399,235

[22] Filed: Mar. 6, 1995

[51] Int. Cl.⁶ ..................................... H04N 7/18
[52] U.S. Cl. .................... 348/88; 348/86; 348/125
[58] Field of Search ........................ 348/88, 86, 8, 348/92, 125, 128, 94; H04N 7/18

[56] References Cited

U.S. PATENT DOCUMENTS

| | | | |
|---|---|---|---|
| 4,172,264 | 10/1979 | Taylor et al. | 348/194 |
| 4,337,482 | 6/1982 | Coutta | 348/143 |
| 4,481,533 | 11/1984 | Alzmann et al. | 348/88 |
| 4,519,041 | 5/1985 | Fant et al. | 364/552 |
| 4,583,181 | 4/1986 | Gerber et al. | 248/88 |
| 4,675,730 | 6/1987 | Adomaitis et al. | 348/88 |
| 4,701,961 | 10/1987 | Hongo | 382/34 |
| 4,737,846 | 4/1988 | Tokuno et al. | 348/143 |
| 4,752,897 | 6/1988 | Zoeller et al. | 364/550 |
| 4,794,453 | 12/1988 | Gnuechtel et al. | 348/132 |
| 4,805,019 | 2/1989 | Holliday | 348/86 |
| 4,814,869 | 3/1989 | Oliver, Jr. | 348/143 |
| 4,941,660 | 7/1990 | Winn et al. | 272/76 |
| 4,951,223 | 8/1990 | Wales et al. | 364/507 |
| 4,955,720 | 9/1990 | Blecha et al. | 356/429 |
| 5,023,714 | 6/1991 | Lemelson | 348/88 |
| 5,034,811 | 7/1991 | Palm | 348/154 |
| 5,073,952 | 12/1991 | Wantanabe | 382/8 |
| 5,113,454 | 5/1992 | Marcantonio et al. | 382/27 |
| 5,134,574 | 7/1992 | Beaverstock et al. | 364/551.01 |
| 5,140,436 | 8/1992 | Blessinger | 386/68 |
| 5,229,850 | 7/1993 | Toyoshima | 348/153 |
| 5,239,376 | 8/1993 | Dittmann et al. | 348/88 |
| 5,365,596 | 11/1994 | Dante et al. | 382/8 |

FOREIGN PATENT DOCUMENTS

| | | | |
|---|---|---|---|
| 0526080 | 2/1993 | European Pat. Off. | G05B 19/417 |
| 2667182 | 3/1992 | France | G06K 9/28 |
| 2 250 156 | 5/1992 | United Kingdom | H04N 7/18 |
| WO 96/27864 | 9/1996 | WIPO | G08B 15/00 |

OTHER PUBLICATIONS

Video Surveillance Trouble Shooting at I.S.P.I. 1994 Engineering Conference p. 531 J.A. DeWitte et al.

*Primary Examiner*—Tommy P. Chin
*Assistant Examiner*—Vu Le

[57] ABSTRACT

The invention is a system for monitoring a process in which process data relating to a predetermined characteristic of the process is collected and stored in digital format and extracted based upon a predetermined criterion for display. A plurality of monitors are strategically positioned at various locations of interest to observe the predetermined characteristic. Data obtained by the monitors are converted into digital format and stored. A central control is provided for retrieving the digital data in accordance with a predetermined criterion and transmitting the retrieved data to a display unit. The predetermined criterion for display may be specified as a deviation from the predetermined characteristic, and a plurality of deviation detectors may be coupled to the system for obtaining and relaying information relating to such deviations. Upon deviation, the central control may be adapted to retrieve digital data based on time and location of the deviation.

19 Claims, 1 Drawing Sheet

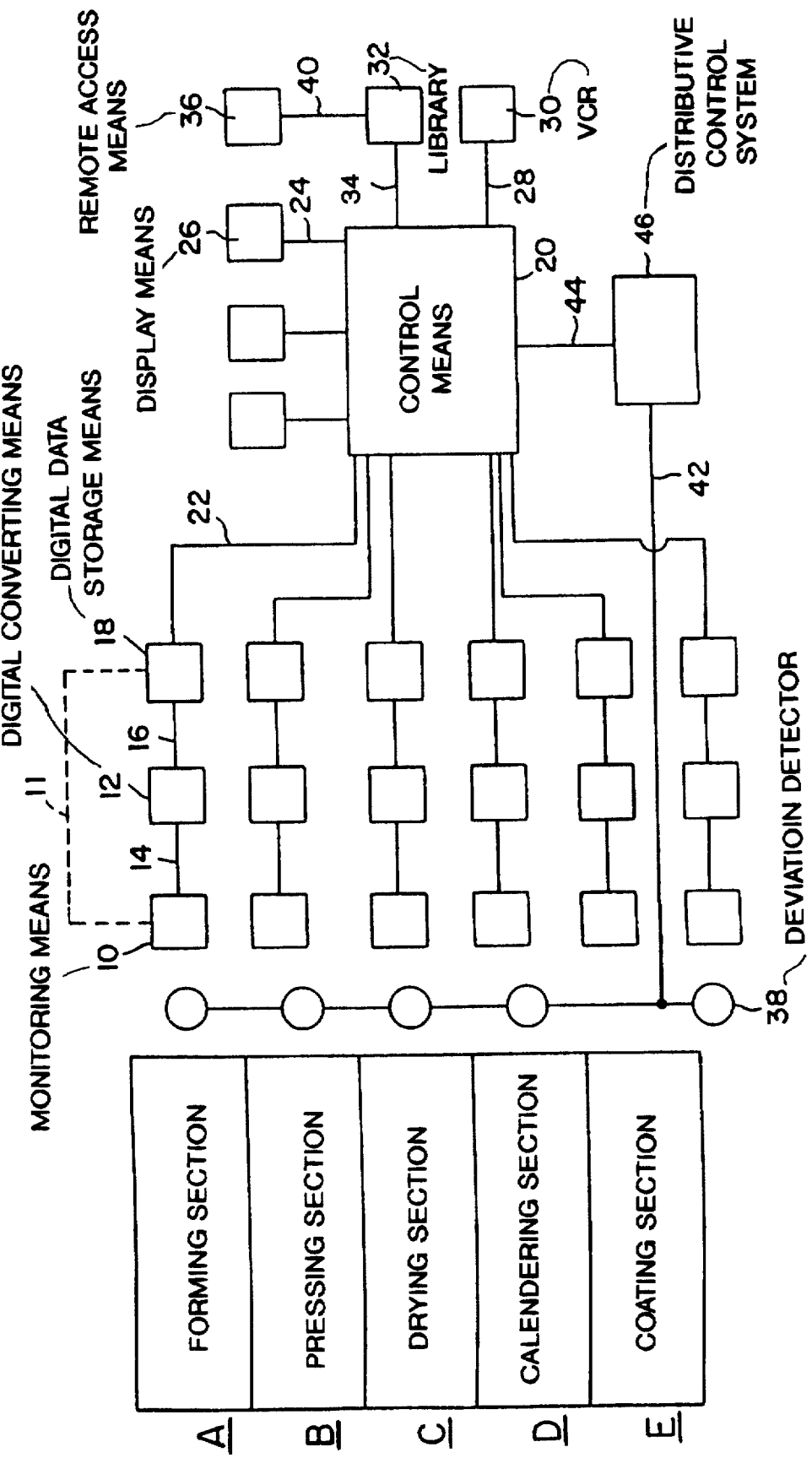

SYSTEM FOR MONITORING A CONTINUOUS MANUFACTURING PROCESS

BACKGROUND OF THE INVENTION

I. Field of the Invention

This invention relates generally to a system for monitoring a process. More particularly, this invention relates to such a system in which process data relating to a predetermined characteristic of the process is collected and stored in digital format and extracted based upon a predetermined criterion for display.

II. Description of the Prior Art

Processes are known for the continuous production or handling of a product. Illustrative of such processes are those for the production or handling of continuous products, as for example polymeric films, paper webs, metallic webs, roll printing processes and the like. Other such processes include those for production or handling of discrete products such as sheet printing processes, packaging processes and the like.

A desired objective of these processes is that the product have certain pre-determined characteristics, as for example characteristics which insure that the product is of acceptable quality. A failure to detect and correct deviations from these pre-determined characteristics is an extreme disadvantage adversely affecting the economics of the process as for example because of lost production time, discarding of unacceptable product, and the like.

As a result, systems for inspecting and observing the product by continuous processes have been developed. See for example the systems described in U.S. Pat. Nos. 4,951,223; 4,814,869; 5,239,376; and the like. These systems usually involve the monitoring through use of one or more video cameras strategically placed along the production line, storage of video output on video tapes, means for shutting down production of the product in the event of deviations from pre-determined characteristics and playback of video tapes to determine the cause of the deviations so that corrections can be made in a timely fashion. These known monitoring systems suffer from one or more disadvantages which adversely affect their performance. For example, these prior processes are manual and require re-winding of the tape which results in down time of the system and long processing times. Moreover, tapes often degrade and it is difficult to access those portions of the tape containing relevant information or to make good copies. In these systems the tapes are not networked or tied together and the system cannot simultaneously recorded and played back. The system of this invention obviates one or more of these disadvantages.

SUMMARY OF THE INVENTION

This invention provides a monitoring system for continuously monitoring the operations of a machine for the continuous manufacture of a product. More particularly, the system of this invention comprises:

- a plurality of monitoring means for continuously monitoring a pre-determined characteristic of the process and collecting monitored data, each monitoring means addressing a different location of interest of said process, and capable of monitoring and collecting real time data relative to said location;
- data converting means for converting said output data into digitized data;
- digital data storage means capable of storing segments of said digitized data, each of said segments comprised of a plurality of digitized data clips, said segments and said clips of predetermined lengths which cover the operations of said process at a relevant location over a predetermined period of time, said digitized data segments being stored such that as new digitized data is stored in said segment, the earliest prior stored digitized data in said segment is displaced from said segment to maintain said segment at said predetermined length; and
- control means for controlling said monitoring system, said control means in communication with said digital data storage means and capable of extracting one or more digitized data clips according to predetermined criterion to form one or more extracted clips, and capable of displaying said extracted clips.

As used herein, "compression" means applying data reduction means such as an appropriate algorithim, technique, technology or the like to digitalized data for a real time event at a location in a process to reduce the amount of digitized data required to recreate the event. As used herein, "process" means an action, change or function or a series of actions, changes or functions that bring about a result or end, as for example a system of operations in the production of something. As used herein, "clip" means a digitalized data series for a location of a process during a pre-determined period of time. As used herein, "digitized" or "digitization" means to convert to or to collect in a digital format as for example conversion of an analog signal of a visual image to a digital format or collection of a visual image directly into a digital format. As used herein, "digital" means information in a binary format, or zeros and ones, usual for storage in a digital data storage means such as a computer. As used herein, "segment" means a portion of the digital data storage means containing one or more digitized data clips.

In a preferred embodiment of the invention, said process is a continuous process for the manufacture of a product, and said deviation event is a deviation in a pre-determined characteristic of said product.

In a more preferred embodiment of the invention, the system comprises a plurality of storage means, each of which comprises at least one digitized data segment, at least one of said storage means capable of storing digitized data monitored and collected from first monitoring means at a first location of the process and at least one of said storage means capable of storing data monitored and collected from a second monitoring means at a second location of the process. Preferably, the control means is capable of extracting clips from segments stored in two or more of said plurality of said storage means such that said extracted clips are time synchronized to chronologically show the pre-determined characteristic of a single discrete product or a portion of a continuous product as said product passes by each location of the digitized data in said extracted clips. Alternatively, the control means is capable of extracting the event clip recording said event and the clip immediately preceding said event clip from the segment containing data from a single location of the process, and optionally the data clip immediately following the event clip, splicing said clips in chronological order to form a display clip and displaying said display clip.

In another preferred embodiment, the process comprises a plurality of steps and wherein there is at least one monitoring means, data converting means and data storage means for said step.

In still another preferred embodiment, the process is controlled by a distributive control system in communication with said control means, said control system having one or more deviation detectors for monitoring said predetermined characteristic, each of said detectors addressing a different location of interest along the process and capable of detecting deviation events and communicating a signal of said deviation event, and the time and location of said event to said control means;

wherein on receipt of said deviation event signal said control means capable of identifying data storage means containing the digitized data segment corresponding to said deviation event, extracting the deviation event clip and displaying said display clip, and wherein said distributive control system is preferably capable of communicating process data relating to the operation of the process and the time of break to said control means.

In yet another preferred embodiment, the control means is capable of extracting the event clip recording said event and the clips immediately preceding and optionally the clip immediately following said event clip, splicing said clips into a display clip chronological order and displaying said display clip.

A most preferred embodiment of this invention relates to a monitoring system for monitoring the manufacture of a continuous web of paper having one or more pre-determined characteristics in a paper manufacturing machine comprising:

a plurality of monitoring means which comprises one or more video cameras for monitoring the paper web, each monitoring means addressing the paper web at a different location of interest along the paper manufacturing machine and capable of producing a video image of the paper web at the location;

digital converting means for converting the video image into a digitized video signal;

digital data storage means capable of receiving said digitized video signal and storing digitized segments thereof, each of which comprises a plurality of digitized clips, said digitized segments and clips of a predetermined length covering real time operation of said machine, said digitized segments being stored such that the earliest prior stored digitized data in said segment is displaced as new digitized data, is stored in said segment to maintain said stored segment at said predetermined length;

Computer control means for controlling the operations of said system, said means in communication with said digital data storage means and capable of controlling same, said computer control means in communication with a distributive control system for controlling said machine, said system having one or more deviation detectors for detecting deviations from predetermined characteristics as said paper web passes through said machine said control system capable of communication process master time and date information to said computer control system; and one or more video monitors in communication with said computer control means and capable of displaying the image of digitized video signals under the control of said computer control means;

wherein on occurrence of a deviation from the predetermined characteristics of said web, said distributive control system transmits a deviation signal comprising the time, date and location of said deviation event to said computer control means, and in response thereto said computer control means identifying the digitized data segment corresponding to said deviation event, extracting the deviation event clip, the preceding clip preceding said break event clip to form a display clip and displaying said display clip on a video monitor.

The system of this invention obviates one or more disadvantages of prior art monitoring systems. For example, There no loss or substantially no loss of data due to rewinding, no or substantially no deterioration in the stored data and good copies of the data can be made. The system can be easily used in an automatic mode an allows simultaneous observation and collection/storage of data. The system allows the monitoring of the process from a central location or from one or more other locations, and allows correlations between collected/recorded data and other process operations data.

BRIEF DESCRIPTION OF THE DRAWINGS

The invention and the advantages attendant thereto will become apparent upon a reading of the following detailed description of the invention taken in conjunction with the accompanying drawings, in which:

FIG. 1 is a depiction of a preferred embodiment of this invention showing a schematic of a paper making machine, including a possible configuration of surveillance cameras and web failure detection devices.

DETAILED DESCRIPTION OF THE INVENTION

The present invention is directed to a system for monitoring a machine or process for manufacture of a product. While the preferred embodiment of FIG. 1 depicts the system in use to monitor a paper manufacturing process and machine. The nature of the process may vary provided that the process has a pre-determined characteristic. The process may be batch, semi-continuous or continuous, or automatic or manual. For example, the process may monitor people or things entering or leaving a building or a room in a building or a process for the manufacture or handling of discrete or continuous products. In the preferred embodiments of the invention, the process is for the manufacture or handling of a product. Processes for manufacturing and handling discrete products include processes for extruding, packaging, filing, bottling, sheet fed printing, conveying, converting, wrapping, stamping, or assembling a discrete product. Process for manufacturing or handling a continuous product include those for the manufacture of a continuous web material such as a polymeric or metal sheet or film, printed paper, carpet, woven material, non-woven material, textile material or photographic film which has certain predetermined characteristics which must not be deviated from. The system can be conveniently used to monitor the manufacture of such continuous or discrete products to monitor for any deviations from the desired pre-determined characteristic(s).

The system is especially useful in paper manufacture as depicted in more detail in FIG. 1. FIG. 1 depicts a schematic representation of a paper making machine in which the wet end forming section is at the top and the final product section is at the bottom. As depicted in the figure, the machine consists of five sections, denoted by A, B, C, D and E. A denotes the forming section; B denotes the pressing section; C denotes the drying section; D denotes the calendaring section; and E denotes the coating section. As shown on FIG. 1, monitoring means 10 are strategically positioned at various locations of interest along the paper making machine. Observing means 10 may vary widely and depends on a pre-determined characteristic of the product being monitored for deviation events. Illustrative of useful observing means are those which employ coherent or non-coherent visual, gamma, infra-red, ultraviolet, thermal and nuclear radiation, sonics, ultrasonics, magnetic fields, pressure, odor and the like. The particular observing means 10 used in any particular situation will normally depend on the pre-determined characteristics of the product being observed and the event which indicates a deviation from the pre-determined characteristic. For example, if the pre-determined characteristic is continuity of the web of paper and the deviation is a break or hole in the web, then monitoring means which employs visual radiation such as a video camera can be conveniently employed. On the other hand, if the pre-determined characteristics are moisture content, surface texture, color, gloss and the like monitoring means which involve the use of visual and infra-red radiation may be used.

In the preferred embodiment of this invention depicted in FIG. 1, monitoring means is a plurality of video cameras 10. While seven cameras 10 are depicted in the figure, the number of cameras employed may vary widely, and any number capable of providing the desired degree of monitoring can be employed. The positioning of various monitoring means 10 may vary widely depending on the needs of the user. In the preferred embodiment depicted in FIG. 1, where the pre-determined characteristic of the web being monitored is web continuity and deviations in this characteristic being detected are break events, hole events or a combination thereof, the number of cameras 10 and camera positions are such that locations where breaks are most likely to occur are covered. For example, as depicted in FIG. 1, cameras 10 are positioned at the drawing section, coating section, size pressing section, center rolls section, sheet pick-up section and reeling device section.

The system of this invention also includes digital converting 12 means for converting data obtained or generated by monitoring means 10 into a digital format. Digital converting means employed may vary widely and any such means capable of performing this function may be used. Illustrative of suitable digital converting means 12 are electronic circuit boards, converting signal processors, video boards, micro-chips, and assorted software. The number of digital converting means 12 and the relationship of digital converting means 10 to monitoring means 10 may vary widely, the only requirement is that relevant monitored data is eventually converted into digital format. For example, there may be a single digital converting means 12 for each monitoring means 10 or there may be one or more digital converting means 12 for all monitoring means 10 or various other combinations of converting means 12 and monitoring means 10 may be employed. Digital converting means 12 and monitoring means 10 may be separate devices as depicted in FIG. 1, or these functions may be performed by the same device as for example a digital video camera 10 which directly monitored data in a digital format, which data is conveyed directly to digital data storage means 18 via conductor 11.

As depicted in FIG. 1, each video camera 10 monitors the web and monitored data is generated in an analog format. The analog data is then conveyed to digital converting means 12 via conductor 14 where the analog data is converted to digital format by digital converting means 12, with or without data compression. The digitized data is then conveyed via conductor 16 to digital data storage means 18.

The specific digital data storage means 18 may vary widely provided that such means allows storage of segments of digitized data having a pre-determined length which covers data obtained by monitoring means 10 which cover the real time operations of the machine over a predetermined period of time. The segment, in turn, is comprised of a plurality of digitized data clips which are also of a pre-determined length which also cover the real time operations of the machine over a predetermined period of time. The segments and clips are in chronological order and are preferably identified by date and time at which the data was collected which greatly facilitates access to relevant data clips on occurrence of a deviation event. Preferably, the clips are also stored such that clips can be readily identified by time and date, and can be extracted or copied from the segment. A further requirement of the digital memory storage means 18 is that it can be controlled by a control means 20 such that specific clips can be extracted from the digital data storage means 18 as desired and as will be described hereinbelow in more detail. In the operations of the digital data storage means 18, the segment is maintained at or about the pre-determined length during the operations of the system such that as new digitized real time data is added to digital data storage means 18, the oldest or most prior data is erased, deleted or otherwise removed from storage means 18 maintaining said segment at or about some pre-determined length. The advantages of this storage means 10 becomes readily apparent in that stored digital data showing normal operations to produce the product having the pre-determined characteristic is constantly removed from storage means 18 such that upon storage of deviating digitized data of a deviation from the pre-determined characteristic, as for example a break event, such deviating data can be more easily isolated from the relatively small amount of data comprising the segment.

The pre-determined length of the segment and the clips may vary widely initially and during the operation of the system, usually depending upon function and capacity of the digital data storage means, duration of the deviation event and the like. The length of the segments are preferably less than about 60 minutes, more preferably from about 15 to about 60 minutes, and most preferably from about 15 to about 30 minutes. The length of the clips comprising a segment is preferably less than about 60 secs., more preferably from about 5 to about 60 secs., more preferably from about 5 to about 20 to 30 secs and most preferably from about 5 to about 10 secs.

The digitized data storage means 18 utilized in any particular situation may vary widely. Illustrative of useful data storage means 18 are hard drive, tape, diskette, CD rom, magnetic optical drive, solid state memory, flash memory, optical device, and the like. Preferred digitized data storage means 18 are hard drives and CD roms. As depicted in FIG. 1, the most preferred digitized data storage means 18 is a hard drive and is in communication with control means 20 by way of connector 22. Control means 20 functions to control the system. Useful control means 20 may vary widely, the only requirement is that means 20 is in the event of a deviation event able to locate the data clip containing data of such event, to extract such data clip and to display said data clip. Illustrative of useful control means 20 are analog control system and a digital computer.

As depicted in FIG. 1, control means 20 is a digital computer which communicates via connector 24 to a plurality of display means 26 which in the embodiment of FIG. 1 are video monitors. Useful display means 26 may vary widely the only is that such means is capable of displaying data to the satisfaction of the operator. Other useful display means 26 are printers, projection systems, photographic imagers and the like. Also connected to control means 20 by way of cable 28 is for example a VCR 30 for recording for wider distribution of data and a library 32 for storage of data by way of cable 34. As depicted in the figure, library 32 can be accessed from various locations by remote access means 36 such as a local area network, wide area network, e-mail services, satellite, compact disk and the like connected to library 32 via cable 40.

FIG. 1 also depicts a plurality of deviation detectors 38 strategic positioned along the machine in a well known manner to detect deviations in the pre-determined characteristics in the product being monitored. Detectors 38 are connected to the machine control or distributive control system 46 via cable 42 for transmission of a deviation signal to system 46. System 46 also communicates with control 20 via cable 44 such that various information can be transmitted to control 20 from system 46 in the event of a deviation from the pre-determined characteristic as for example a break in a web. Such information includes the detection of a deviation event, time of detection of the deviation event and such other process data relating to the operations of the machine at the time of deviation event deemed appropriate.

In operation, monitoring means 10 continuously monitors a pre-determined characteristic of the product being produced by the machine. The monitored data is conveyed via cable 14 to digital conversion means 12 where the data is converted to a digital format, and the digitized data is conveyed to digital data storage means 18 via cable 16 for storage. In those embodiments of the invention where the monitored data is collected in digital format by monitoring means 10, as for example by a digital video camera, the digitized data is converted directly to digital data storage means 18 via cable 11. During operations where there are no deviations from the pre-determined characteristics, digitized data flows continuously into storage means 18 such that only a pre-determined amount of data converting a pre-determined period of time during the operation of the machine is always maintained in storage and that as new data is stored the oldest or most prior data is deleted or erased.

If a deviation in the pre-determined characteristics of the product occurs, it is detected by a deviation detector 38. Detector 38 sends a deviation signal to distributive control system 46 via cable 42, and the signal is relayed to control means 20 via cable 44. In addition to a deviation signal, detector 38 may also inform control system 40 of the identity of detector 38 detecting the deviation event, the time of the deviation event and location in the process of the deviation event. This information together with other process data such as type of product being manufactured, machine operation parameters, machine speed, draw ratios, furnish, types, additives, coating components, calendaring pressures, coating thickness, basis weight of the paper and the like are conveyed to control means 20. On receipt of the deviation event signal, control means 20 is capable of identifying the clip most likely to have digitized data relating to the deviation event, and extracting such clip and displaying the extracted clip with display means 26. For example, control means 20 can perform this function by coordinating the time at which deviation event detector 38 detected the deviation event with the clip or clips corresponding in time. This coordination can be done in any suitable manner. For example, control 20 can scan all digitized data storage means 18, select clips from all means 18 containing data collected at the appropriate time and can then scan each clip to identify the deviation event and display same. Alternatively, control means 20 can identify the monitoring means 10 most proximate to the location of the deviation event, select a clip or clips from the digitized data storage means 18 for such monitoring means 10 and display such clip. In order to insure that all suitable data is displayed in the fastest possible time, preferably control means 20 will also extract digitized data clips immediately preceding and following the clip or clips most likely containing data for the deviation event and will splice the deviation event clip and the following and preceding clips into a display clip for display. By splicing the event, preceding and following clips, She operation of the machine prior to, during and subsequent to the deviation event can be observed. After a deviation is detected, the machine is usually stopped and the digitized data storage means 18 is frozen to prevent loss of critical data.

The clips can be displayed automatically or manually at any suitable speed. The clips can be displayed frame by frame, in various sizes. The clips can also be viewed in reversed mode. This function combined with a pause, playback and resizing can enhance the ability of the operators to locate the exact point of interest on the display clip, for study showing the deviation event as it occurred. Of course, many other functions may be provided by control means 20 including zooming, edge enhancement, image sharpening, gradient edge enhancement, de-specking, filtering, cropping, desizing, dithering, interpolation, image intensity, format conversion, color inversion, contrast control, brightness control, embossing and the like. Manual/automatic control of all functions may be provided.

In this manner, the control means 20 becomes the driver which also manages the logistics of the system including monitoring, displaying, storage, etc., and can additionally be used to supervise the status of each device in the system as desired. In addition, other peripherals can be provided as needed.

The ability to review the critical period just prior to the deviation event at any desired speed provides the input necessary to evaluate the cause of the problem so that necessary adjustments and/or repairs can be started quickly and the machine restored to normal operation. If only a defect in the product is to blame, this, too, often will show up. In this manner, valuable time can be saved.

The clip or clips covering the deviation event are displayed, the cause of the deviation event can be discovered and appropriate action can be taken to correct the cause of the event. The process or machine and the monitoring system can then be reactivated.

The clips relating to the deviation event together with any other process data associated with the deviation event are conveyed via line 34 to library 32 for storage. In this manner, a collection of deviation clips and associated process data is formed which can be accessed by remote access 36 via connector 40 for suitable purposes as for example for accessing, and correlating or otherwise evaluating accessed data based on or more variables such as process times, properties, products, types or modes of deviation events, recorded observations, types of machines, and like process or product characteristics, and to document machine or process defects such as a hole in the felt or wire. The clips and associated process data may also be conveyed via connector 28 to video recorder 30 for storage on a video tape.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications both as to equipment and procedure details can be accomplished without departing from the scope of the invention.

What is claimed is:

1. A monitoring system for monitoring the manufacture of a continuous web of paper having one or more predetermined characteristics in a paper manufacturing machine comprising:

a plurality of monitoring means which comprises one or more video cameras for monitoring the paper web, each monitoring means addressing the paper web at a different location of interest along the paper manufacturing machine and for producing a video image of the paper web at the location;

digital converting means for converting the video image into a digitized video signal;

digital data storage means for receiving said digitized video signal and storing digitized segments thereof, each of which comprises a plurality of digitized clips, said digitized segments and clips of a predetermined length covering real time operation of said machine, said digitized segments being stored such that earlier prior stored digitized data in said segment is removed as new digitized data is stored in said segment to maintain said stored segment at or about said predetermined length;

computer control means for controlling the operations of said monitoring system, said means in communication with said digital data storage means, said computer control means in communication with a distributive control system for controlling said machine, said control system having one or more deviation detectors for detecting deviations from predetermined characteristics as said paper web passes through said machine; and one or more video monitors in communication with said computer control means and for displaying the image of digitized video signals under the control of said computer control means;

wherein an occurrence of a deviation from the predetermined characteristics of said web, said distributive control system transmits a deviation signal comprising the time, date and location of said deviation event to said computer control means, and in response thereto said computer control means identifying the digitized data segment corresponding to said deviation event, extracting the deviation event clip, the preceding clip preceding said break event clip to form a display clip and displaying said display clip on a video monitor.

2. System of claim 1 wherein at least one digital converting means is in communication with at least one video camera and at least on digital data storage means is in communication with at least one digital converting means.

3. System of claim 2 wherein on receipt of said deviation event signal at the time of said deviation, said computer control means identifies a video camera proximate to said deviation detector detecting said deviation event, freezes operations of digital memory storage means for such camera, identifies the digitized data segment corresponding to said deviation event by correlating the time of said segment with the time of said deviation event, extracting the deviation event clip which correlates to the time of said deviation event and the preceding clip preceding said deviation event clip and the subsequent clip following said deviation event clip, splicing said deviation event clip, said preceding clip and said subsequent in chronological order to form a display clip and displaying said display clip on said video monitor.

4. System of claim 3 which further comprises:

means for transmitting process data from the distributive control system with said break event signal;

library means for storage of display clips and associated process data; and means for accessing said display clips and process data stored in said library.

5. System of claim 1 wherein said event is selected from the group consisting of a break in said web, a hole in said web and a change in a surface characteristic of said web.

6. System of claim 1 wherein said computer control means is also for controlling said digital data storage means.

7. System of claim 1 wherein said distributive control system is also for communicating process master time and date information to said computer control system.

8. A monitoring system for continuously monitoring a process for the manufacture of a product, said process comprising:

a plurality of monitoring means for continuously monitoring a pre-determined characteristic of the process and collecting monitored data, each monitoring means addressing a different location of interest of the process, and each said monitoring means for monitoring and collecting data in real time relative to said location;

data converting means for converting said collected data into digitized data;

digital data storage means for storing segments of said digitized data, each of said segments comprised of one or more digitized data clips, said segments and said clips of pre-determined lengths which cover the operations of said process at a relevant location over a pre-determined period of time, said digitized data segments being stored such that as new digitized data is stored in said segment, earlier prior stored digitized data in said segment is removed from said segment to maintain said segment at or about said pre-determined length;

a distributive control system for controlling the process, said control system having one or more deviation detectors for monitoring said pre-determined characteristic and for detecting deviation events in said pre-determined characteristic, each of said detectors addressing a different location of interest along the process and for transmitting a signal of said deviation event, and the time and location of said event; and control means in communication with said control system and said digital data storage means, said control means for controlling said monitoring system and for extracting one or more digitized data clips on receipt of said deviation event signal to form one or more extracted clips, said control means also for identifying data storage means containing said digitized data segment corresponding to the time and the location of said deviation event, for extracting said deviation event clip to form a display clip and for displaying said display clip.

9. System of claim 8 wherein said process is a continuous process for the manufacture of a product.

10. System of claim 9 wherein said process comprises a plurality of steps and wherein there is at least one monitoring means for each of said steps.

11. System of claim 8 wherein a plurality of monitoring means address a single location, each in communication with a digital data converting means which is in communication with a digital data storage means, said control means extracts one or more digitized data clips from each of said storage means and displays said extracted clips.

12. A system of claim 11 wherein each of said monitoring means monitors a different pre-determined characteristic.

13. A system of claim 12 wherein said monitoring means are different.

14. System of claim 8 wherein said distributive control system is also for communicating process data relating to the operation of the process to said control means.

15. System of claim 14 which further comprises:
library means in communication with said control means for storage of display clips and process data relating to the operation of the machine at the time of deviation, said library also for display of said stored display clips and process data.

16. System of claim 15 wherein said control means extracts the event clip recording said event and the clip immediately preceding said event clip, splicing said clips in chronological order to form a display clip and displaying said display clip.

17. System of claim 16 wherein said control means extracts the event clip recording said event, the clip immediately preceding said event clip, the clip immediately following said event clip, splicing said clips in chronological order to form a display clip and displaying said display clip.

18. System of claim 8 wherein said pre-determined criterion is a deviation event in which there is a deviation in said pre-determined characteristic.

19. System of claim 8 wherein the process is a continuous process for the manufacture of a product.

* * * * *